(12) United States Patent
In

(10) Patent No.: US 9,164,489 B2
(45) Date of Patent: Oct. 20, 2015

(54) WATCH WITH COUNTERFEIT DETECTION FUNCTION

(71) Applicant: Seoul Viosys Co., Ltd., Ansan-si (KR)

(72) Inventor: Chi Hyun In, Ansan-si (KR)

(73) Assignee: SEOUL VIOSYS CO., LTD., Ansan-Si (KR)

( * ) Notice: Subject to any disclaimer, the term of this patent is extended or adjusted under 35 U.S.C. 154(b) by 0 days.

(21) Appl. No.: 14/514,243

(22) Filed: Oct. 14, 2014

(65) Prior Publication Data

US 2015/0103634 A1    Apr. 16, 2015

(30) Foreign Application Priority Data

Oct. 14, 2013 (KR) .................. 10 2013 0121812

(51) Int. Cl.
*G04B 47/06* (2006.01)
*G04B 47/00* (2006.01)
*G04B 19/06* (2006.01)
*G01N 21/64* (2006.01)

(52) U.S. Cl.
CPC ............ *G04B 47/00* (2013.01); *G01N 21/6447* (2013.01); *G04B 19/06* (2013.01)

(58) Field of Classification Search
CPC ........ G04B 19/32; G04B 19/30; G04B 47/00; G04B 19/06; G04D 3/0069; A01B 12/006; G01N 21/6447

USPC ........................................... 368/226
See application file for complete search history.

(56) References Cited

U.S. PATENT DOCUMENTS

| | | | | |
|---|---|---|---|---|
| 3,293,846 A * | 12/1966 | Pauli | ............................... | 368/10 |
| 4,095,414 A * | 6/1978 | Reich | .............................. | 368/83 |
| 4,413,915 A * | 11/1983 | Besson | ............................ | 368/71 |
| 4,444,513 A * | 4/1984 | Proellochs et al. | ........... | 368/223 |
| 4,575,833 A * | 3/1986 | Bakhtiari | ...................... | 368/282 |
| 5,032,711 A * | 7/1991 | Yamada | .................... | 250/461.1 |
| 5,479,381 A * | 12/1995 | Goldenberg et al. | ......... | 368/282 |
| 5,604,716 A * | 2/1997 | Cheung | ........................... | 368/67 |
| 6,806,644 B2 * | 10/2004 | Ueno et al. | .................... | 313/512 |
| 6,944,098 B2 * | 9/2005 | Rochat et al. | ................... | 368/88 |
| 7,221,044 B2 * | 5/2007 | Fan et al. | ...................... | 257/676 |
| 2004/0213088 A1 * | 10/2004 | Fuwausa | ..................... | 368/228 |
| 2006/0013074 A1 * | 1/2006 | Ueno et al. | .................... | 368/226 |
| 2010/0202255 A1 * | 8/2010 | Klopfenstein et al. | ........ | 368/226 |

FOREIGN PATENT DOCUMENTS

KR    1020020010163 A    4/2002

* cited by examiner

*Primary Examiner* — Sean Kayes
(74) *Attorney, Agent, or Firm* — Perkins Coie LLP

(57) ABSTRACT

A wearable device such as a watch with a counterfeit detection function that include a display panel configured to display information (e.g., time); a UV LED unit arranged at an edge part of the display panel and configured to provide UV light which reacts with a fluorescent material; and a transparent cover positioned over the display panel so as to focus the UV light.

17 Claims, 4 Drawing Sheets

WATCH WITH COUNTERFEIT DETECTION FUNCTION

CROSS-REFERENCES TO RELATED APPLICATIONS

This patent document claims the priority to and the benefits of Korean application number 10-2013-0121812, filed on Oct. 14, 2013, which is incorporated by reference in its entirety.

BACKGROUND

The disclosure of this patent document relates to a watch or a wearable device with a counterfeit detection function.

Recently, the demand for technology related to an anti-counterfeit function for determining authenticity of paper currency bills has increased. Conventionally, a technique for adding a specific fluorescent pattern to a paper currency bill as a way of determining the authenticity of the bill has been applied to a process of manufacturing a bill, in order to distinguish between a counterfeit bill and a real or authentic bill based on presence or absence of such a fluorescent pattern. When ultraviolet (UV) light is irradiated onto the real bill, the real bill reacts with the irradiated UV light such that the fluorescent pattern emits light. However, a counterfeit bill that does not have such a fluorescent pattern would not react with the irradiated UV light in the way an authentic or genuine bill would.

As an example of a conventional counterfeit detector, Korean Patent Application No. 10-2000-0043258, which was published under KR20020010163 (A), has disclosed a handy or portable detector for detecting forged notes or counterfeit bills. The disclosed counterfeit detector in the above Korean document includes a main body; a naked-eye identification unit for identifying a character or pattern with the naked eye; an electronic detection unit for irradiating UV light and detecting the UV light reflected or transmitted from a bill so as to determine whether the bill is counterfeit; and a magnetic detection unit for detecting magnetic ink of the bill passing through a bill passing groove formed in the main body.

Recently, there is an increasing need for more people to determine whether a bill is counterfeit or genuine. In particular, with the increase of overseas travel, people need to check whether a bill is counterfeit or genuine when they stay in a foreign country in which counterfeit bills are likely to be distributed. Thus, although handy or portable counterfeit detectors have emerged, there is a continuous demand for a convenient and portable counterfeit detector.

SUMMARY

Embodiments of the technology disclosed in this patent document are directed to a watch or a wearable device with a counterfeit detection function, which can be simply manipulated and conveniently or easily carried around by a person.

In one embodiment, a watch with a counterfeit detection function may include: a display panel configured to display time information; a UV light emitting diode (LED) unit arranged at an edge part of the display panel and configured to provide UV light which reacts with a fluorescent material embedded in a pattern in an object to cause the fluorescent material to emit fluorescent light as an indication of the object being authentic in counterfeit detection; and a transparent cover positioned over the display panel so as to transmit and focus the UV light.

In another embodiment, a watch with a counterfeit detection function may include: a main body comprising a display panel that displays information including time and a support board arranged at an edge part of the display panel; and two or more UV LED units arranged on different surfaces of the support board and configured to irradiate UV light in different directions, the UV light reacting with a fluorescent material embedded in a pattern in an object to cause the fluorescent material to emit fluorescent light as an indication of the object being authentic in counterfeit detection.

In another embodiment, a watch with a counterfeit detection function may include: a digital display panel that displays digital information including time; a support coupled to support the display panel; UV LED units mounted on the support and located outside the digital display panel, each UV LED unit operable to emit UV light at a wavelength that reacts with a fluorescent material embedded in a pattern in an object to cause the fluorescent material to emit fluorescent light as an indication of the object being authentic in counterfeit detection; and a controller mounted to a side of the support and coupled to control operations of the digital display and the UV LED units.

In still another embodiment, a method for performing counterfeit detection of currency bills by using a wearable device is provided. In the method, one or more LED units in the wearable device are operated to emit UV light at a wavelength that reacts with a fluorescent material embedded in a pattern in an object to cause the fluorescent material to emit fluorescent light as an indication of the object being authentic in counterfeit detection. A controller of the wearable device is controlled to turn on the one or more LED units to activate the counterfeit detection, and to turn off the one or more LED units to turn off the counterfeit detection.

In yet another embodiment, the disclosed technology provides a method for performing counterfeit detection of currency bills by using a wearable device. This method includes operating one or more LED units in the wearable device to emit UV light at a wavelength that reacts with a fluorescent material embedded in a pattern in an object to cause the fluorescent material to emit fluorescent light as an indication of the object being authentic in counterfeit detection; and controlling a controller of the wearable device to turn on the one or more LED units to activate the counterfeit detection, and to turn off the one or more LED units to turn off the counterfeit detection.

In accordance with embodiments or implementations of the disclosed technology, the UV LED unit which can be reduced in size and have excellent durability and low power consumption may be arranged in the watch, instead of a UV lamp used in the conventional counterfeit detector. Thus, a user may easily detect a counterfeit bill.

Furthermore, as the UV LED unit for counterfeit detection is arranged in the watch, it is possible to provide the counterfeit detector which has excellent portability and is conveniently used.

DESCRIPTION OF SPECIFIC EMBODIMENTS

Figure 1A:
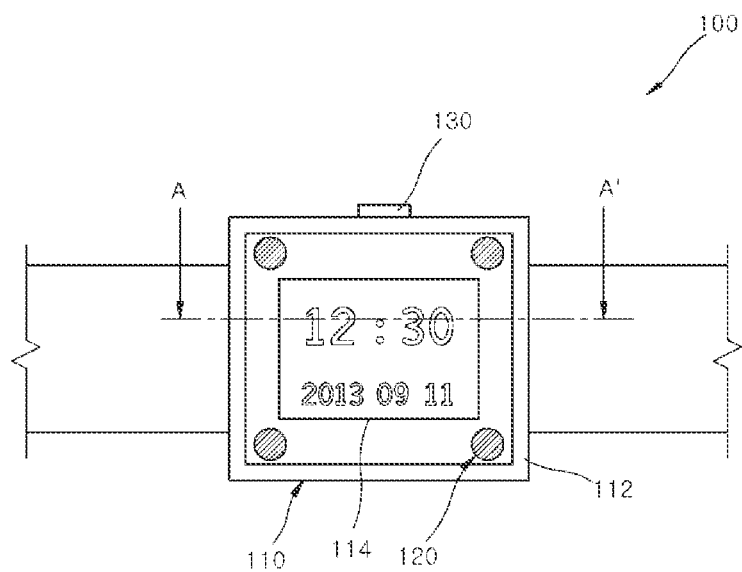
FIG. 1A is a schematic plan view of an example of a watch with a counterfeit detection function in accordance with a first embodiment of the disclosed technology.

Embodiments of the disclosed technology will hereinafter be described in detail with reference to the accompanying drawings. It should be noted that the drawings are not to precise scale and may be exaggerated in some aspects, e.g., in thickness of lines or sizes of certain components, for descriptive convenience and clarity only.

In embodiments of the disclosed technology, when an element is referred to as being positioned on another element or over, under, and at a side of another element, it may indicate the relative positional relationship therebetween. Thus, the former element may be directly contacted with the latter element, or an additional element may be interposed at the interface therebetween. Furthermore, when an element is referred to as being coupled or connected to another element, it may indicate that the former element is directly coupled or connected to the latter element or an additional element is interposed therebetween. Throughout the specification, like reference numerals denote substantially the same components.

Figure 1B:
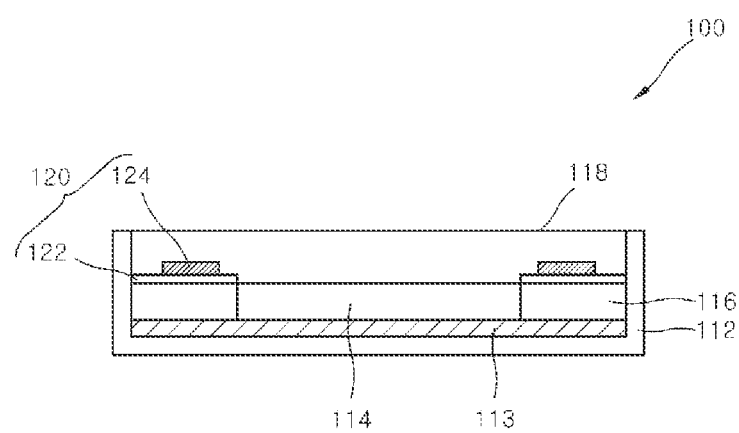
FIG. 1B is a cross-sectional view of the watch with a counterfeit detection function, taken along line A-A' of FIG. 1.

FIG. 1A is a schematic plan view of an example of a watch with a counterfeit detection function in accordance with a first embodiment of the disclosed technology. FIG. 1B is a cross-sectional view of the watch with a counterfeit detection function, taken along line A-A' of FIG. 1.

Referring to FIGS. 1A and 1B, the watch 100 with a counterfeit detection function includes a main body 110 and a UV LED unit 120 for providing or generating UV light which reacts with a fluorescent material. Furthermore, the watch 100 may further include a controller 130 arranged on a sidewall of the main body 110 so as to control the operation of the UV LED unit 120. As illustrated, the UV LED unit 120 may include LEDs that collectively generate the desired UV light, e.g., four LEDs distributed at peripheral locations of the watch 100 in FIG. 1A.

Referring to FIGS. 1A and 1B, the main body 110 may include a main body frame 112, an electronic arithmetic unit 113, a display panel 114, and a support board 116. The main body frame 112 forms the exterior of the main body 110. FIGS. 1A and 1B illustrate that the main body frame 112 has a rectangular shape in the illustrated example. However, the main body frame 112 is not limited to the rectangular shape and may be in various other shapes.

The electronic arithmetic unit 113 serves to perform an operation related to time and determine the current time. The display panel 114 can display the time and date information calculated through the electronic arithmetic unit 113. FIG. 1A illustrates a digital electronic watch, for example, where the display panel 114 is a digital display panel to display digital information including digits for time information such as "12:30" for displaying time and "2013 09 11" for displaying the calendar date as shown. Additional digital information may also be displayed on the display panel 114. The electronic arithmetic unit 113 may include a power supply device for supplying power to the watch. The power supply device may include a mercury cell, a battery or a suitable portable power supply device.

The support board 116 may be arranged at an edge part of the display panel 114. In a specific embodiment, the UV LED unit 120 may include a printed circuit board 122 arranged on the top surface of the support board 116 and a UV LED package 124 mounted on the PCB 122. The UV LED package 124 may include a package board and a UV LED chip coupled to the package board through a flip chip process in a flip chip configuration or structure. In another embodiment, the UV LED chip may be directly mounted on the PCB 122 without the package board. The UV LED chip may provide UV light at a wavelength of about 300 nm to 420 nm.

Currently, in many countries including Korea, the material for a bill paper is mixed with a cotton or chemical fiber colored with a fluorescent material. The fluorescent material can react with UV light to emit fluorescent light so as to identify the real bill. In implementing the disclosed technology, a user may determine whether a fluorescent material exists within a target bill, using UV light provided from the UV LED unit 120 for counterfeit detection. Then, the user may determine whether the target bill is a real bill or counterfeit bill.

A transparent cover 118 may be attached to the top of the main body 110 and to allow the emitted UV light from the underlying the UV LED unit 120 to pass through. The transparent cover 118 may serve as a lens for focusing or spreading the propagation direction of UV light emitted from the UV LED unit 120. As described above, the transparent cover 118 may be positioned over the display panel 114 and serve as a lens for focusing UV light. At this time, a part of the transparent cover 118 may be manufactured to have surface roughness such that the transparent cover 118 has a lens function.

In the illustrated example in FIG. 1A, the controller 130 is disposed at a sidewall of the main body 110. A user may manipulate the controller 130 to correct the time or date information. In addition, a user may manipulate the controller 130 to turn on or off the UV LED unit 120 for counterfeit detection. Furthermore, a user may manipulate the controller 130 to control the intensity of light emitted from the UV LED unit 120 for counterfeit detection. In an embodiment, the operation of turning on or off the UV light may be performed by controlling power supply to the UV LED unit 120 for counterfeit detection. Furthermore, the light intensity control may be performed as follows: a variable resistor is arranged on a driving circuit of the UV LED unit 120 for counterfeit detection, and the resistance of the variable resistor is adjusted to control the amount of current provided to the UV LED unit 120.

In accordance with the embodiment of the disclosed technology, the UV LED unit 120 may be arranged in the watch and operated as a detection device. The UV LED unit 120 may be reduced in size and have excellent durability and low power consumption, compared to a UV lamp applied to the conventional counterfeit detector. Thus, the UV LED unit 120 may be easily embedded in a portable device such as a watch.

Thus, when a user travels around a country in which counterfeit bills are likely to be distributed, the user may easily determine whether a bill is counterfeit or not, using the watch in accordance with the embodiment of the disclosed technology, without a separate counterfeit detector.

Figure 2A:
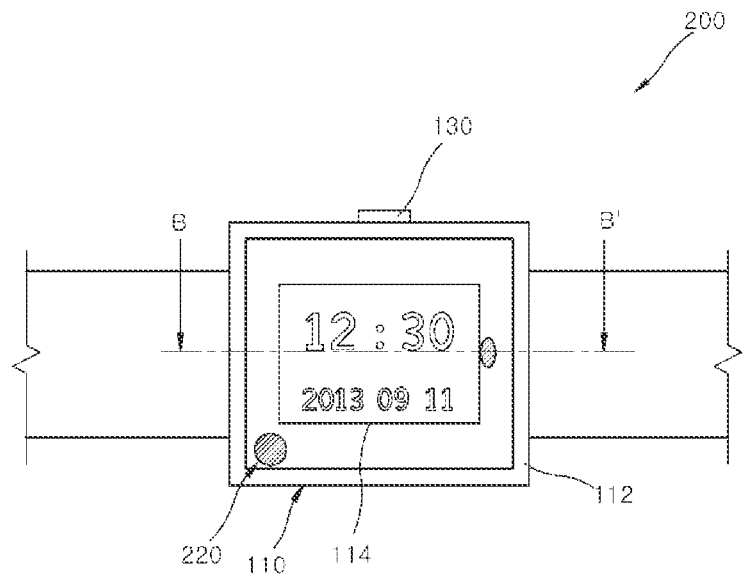
FIG. 2A is a schematic plan view of an example of a watch with a counterfeit detection function in accordance with a second embodiment of the disclosed technology.
Figure 2B:
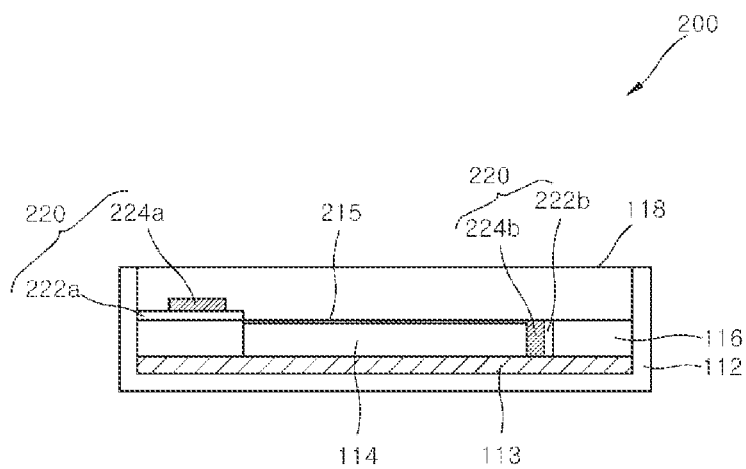
FIG. 2B is a cross-sectional view of the watch with a counterfeit detection function, taken along line B-B' of FIG. 2A.

FIG. 2A is a schematic plan view of an example of a watch with a counterfeit detection function in accordance with a second embodiment of the disclosed technology. FIG. 2B is a cross-sectional view of the watch with a counterfeit detection function, taken along line B-B' of FIG. 2A.

Referring to FIGS. 2A and 2B, the watch 200 with a counterfeit detection function includes a main body 110 and a UV LED unit 220 for counterfeit detection. Specifically, the watch 200 with a counterfeit detection function may include two or more UV LED units 220 which are arranged on different surfaces of the support board 116 and irradiate or emit UV light in different directions, the UV light reacting with a fluorescent material. Furthermore, the watch 200 may further include a controller 130 arranged on a sidewall of the main body 100 so as to control the operations of the UV LED units 220.

The watch 200 with a counterfeit detection function in accordance with the embodiment of the disclosed technology may have substantially the same configuration as the watch 100 described with reference to FIGS. 1A and 1B, except for the configuration of the UV LED unit 220 for counterfeit detection. Thus, the following descriptions will be focused on the difference in FIGS. 2A and 2B from FIGS. 1A and 1B, in order to exclude duplicate description.

Referring to FIGS. 2A and 2B, a UV LED unit 220 for counterfeit detection includes a first PCB 222a arranged on the top surface of the support board 116 and a first UV LED package 224a mounted on the first PCB 222a. The first UV LED package 224a may include a package board and a first UV LED chip coupled to the package board through a flip chip process in a flip chip configuration or structure. In another embodiment, the first UV LED chip may be directly mounted on the first PCB 222a without the package board. The first UV LED chip may provide UV light at a wavelength of about 300 nm to 420 nm. As illustrated in this specific example, the first UV LED package 224a may be configured to emit the UV light upward in FIG. 2B.

Furthermore, another UV LED unit 220 for counterfeit detection includes a second PCB 222b arranged on a side surface of the support board 116 and a second UV LED package 224b mounted on the second PCB 222b. The second UV LED package 224b may include a package board and a second UV LED chip coupled to the package board through a flip chip process in a flip chip configuration or structure. In another embodiment, the second UV LED chip may be directly mounted on the second PCB 222b without the package board. The second UV LED chip may provide UV light at a wavelength of about 300 nm to 420 nm.

In the present embodiment, as illustrated in FIG. 2B, the second UV LED package 224b may be configured to emit the UV light in a direction towards the right side in FIG. 2B, different from the upward light direction of the UV light emitted by the first UV LED package 224a. In operation, the first UV LED chip may emit UV light for counterfeit detection toward the top of the watch. Thus, a user may irradiate the UV light from the first UV LED chip onto a target bill, and determine whether the target bill is counterfeit or not. Furthermore, the second UV LED chip may emit the UV light toward the display panel 114, and perform the function of a lighting device for illumination, and, in addition, the second UV LED chip may also provide the UV light for counterfeit detection to increase the intensity of UV light with the first UV LED chip. The inclusion of both the first UV LED chip and the second UV LED chip that emit UV light in two different directions provides two different functions and convenience to the user.

In a specific embodiment, the second UV LED chip for illumination may be referred to as a black light, for example, and emit UV light in a wavelength region close to the visible light region, the UV light easily reacting with a fluorescent material. Correspondingly, the display panel 114 may include a fluorescent material 215 reacting with the UV light from the second UV LED chip. In response to the UV light emitted from the second UV LED chip, the fluorescent material 215 in the display panel 114 may emit light in the visible light region such that a user can read information of the display panel 114 under the illumination of the emitted visible light from the fluorescent material in the display panel 114. The fluorescent material 215 may be applied onto at least a part of the display panel 114.

According to a user's selection, the second UV LED chip may be turned on/off separately from the first UV LED chip, and the light intensity of the second UV LED chip may be controlled separately from that of the first UV LED chip. Thus, when the function of the lighting device for illumination is desired and activated, only the second UV LED chip may be operated to emit light. Similarly, when the function of the counterfeit detection device is requested, only the first UV LED chip may be operated to emit light.

Figure 3A:
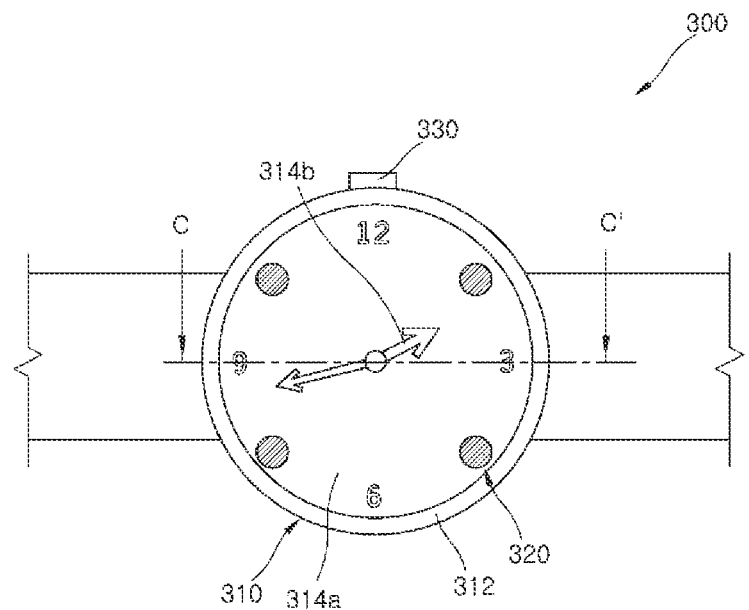
FIG. 3A is a schematic plan view of an example of a watch with a counterfeit detection function in accordance with a third embodiment of the disclosed technology.
Figure 3B:
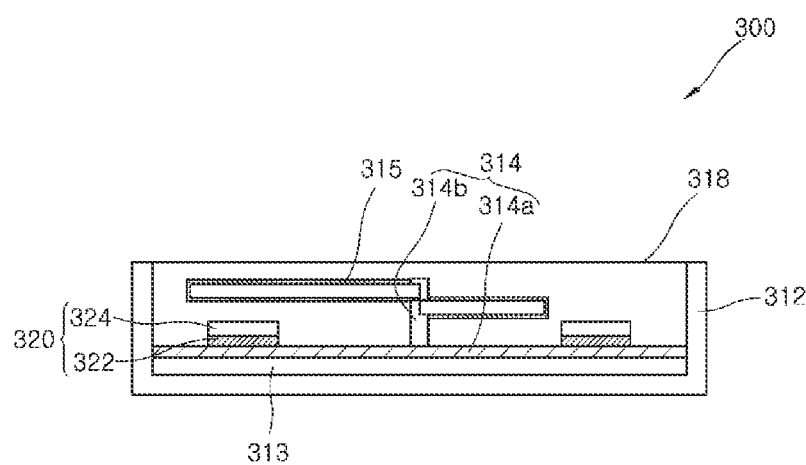
FIG. 3B is a cross-sectional view of the watch with a counterfeit detection function, taken along line C-C' of FIG. 3A.

FIG. 3A is a schematic plan view of an example of a watch with a counterfeit detection function in accordance with a third embodiment of the disclosed technology. FIG. 3B is a cross-sectional view of the watch with a counterfeit detection function, taken along line C-C' of FIG. 3A.

Referring to FIGS. 3A and 3B, the watch 300 with a counterfeit detection function includes a main body 310 and a UV LED unit 320 for counterfeit detection. In implementations, more than one UV LED unit 320 may be used, e.g., four UV LED units 320 for counterfeit detection as shown in FIG. 3A. Furthermore, the watch 300 may further include a controller 330 arranged on a sidewall of the main body 310 so as to control the operation of the UV LED unit 320.

Referring to FIGS. 3A and 3B, the main body 310 includes a main body frame 312, a mechanical driving unit 330, and a display panel 314. The main body frame 312 forms the exterior of the main body unit 310. The main body frame 312 may include a bottom part and a sidewall part. The main body frame illustrated in the drawings has a circular shape in its exterior. However, the main body frame is not limited to a circular shape and may be in various other exterior shapes.

The mechanical driving unit 330 includes a mechanism related to the operation of the watch, and operates the hour hand, the minute hand, and the second hand of the watch to display time.

The display panel 314 is arranged over the bottom part of the main body frame 312 so as to display the time information. Specifically, the display panel 314 includes a number board 314a and clock hands 314b arranged on the number board 314a.

The UV LED unit 320 for counterfeit detection may be arranged on the main body frame 312. In a specific embodiment, the UV LED unit 320 for counterfeit detection includes a PCB 322 arranged on the bottom part and a UV LED package 324 mounted on the PCB 322. The UV LED package 324 may include a package board and a UV LED chip coupled to the package board through a flip chip process in a flip chip configuration or structure. In another embodiment, the UV LED chip may be directly mounted on the PCB 322 without the package board. The UV LED chip may provide UV light at a wavelength of about 300 nm to 420 nm.

In some embodiments, the clock hands 314b may be coated with a fluorescent material 315. In response to the UV light emitted from the UV LED unit 320 for counterfeit detection, the fluorescent material 315 may emit light in the visible region such that the UV LED unit 320 performs the function of a lighting device for illumination.

A transparent cover 318 and a controller 330 may have substantially the same configuration as the transparent cover 118 and the controller 130 of the watch 100, which have been described with reference to FIGS. 1A and 1B. In addition, the watch 300 can also include an electronic arithmetic unit 313 similar to the electronic arithmetic unit 113 described with reference to FIGS. 1A and 1B.

Figure 4A:
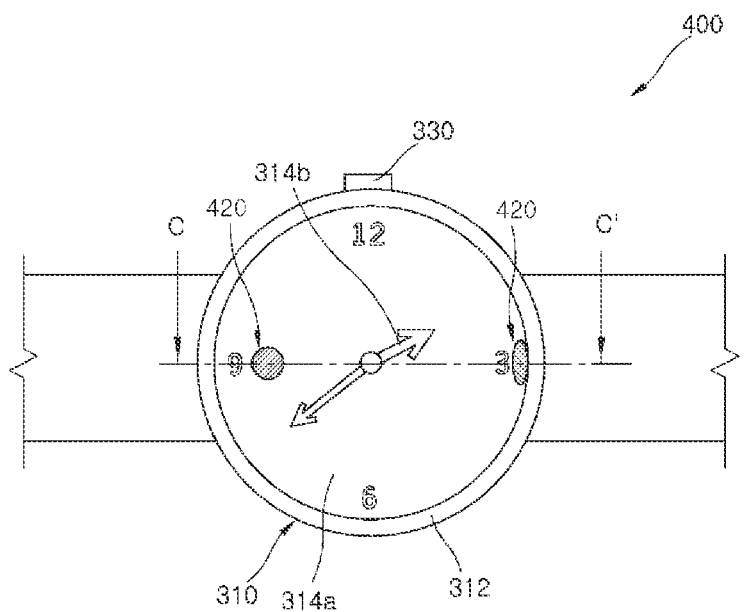
FIG. 4A is a schematic plan view of an example of a watch with a counterfeit detection function in accordance with a fourth embodiment of the disclosed technology.
Figure 4B:
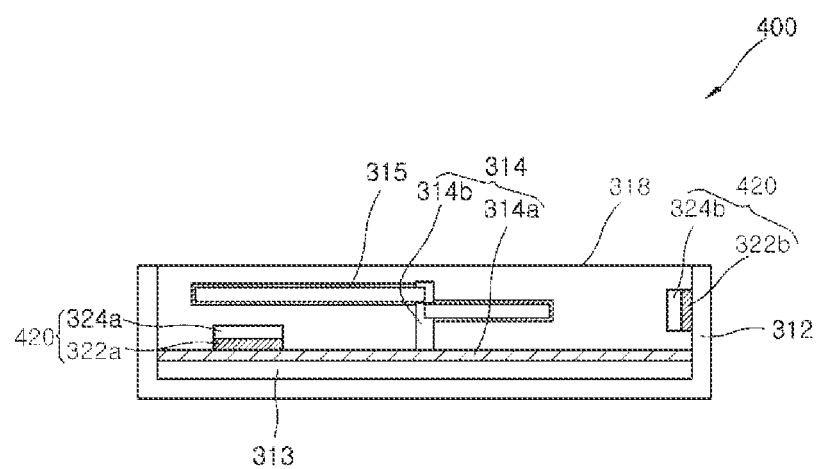
FIG. 4B is a cross-sectional view of the watch with a counterfeit detection function, taken along line D-D' of FIG. 4A.

FIG. 4A is a schematic plan view of an example of a watch with a counterfeit detection function in accordance with a fourth embodiment of the disclosed. FIG. 4B is a cross-sectional view of the watch with a counterfeit detection function, taken along line D-D' of FIG. 4A.

Referring to FIGS. 4A and 4B, the watch 400 with a counterfeit detection function includes a main body 310 and two or more UV LED units 420 for counterfeit detection. The watch 400 may further include a controller 330 arranged on a sidewall of the main body 310 so as to control the operation of the two or more UV LED units 420.

The watch 400 with a counterfeit detection function in accordance with the embodiment as shown may have substantially the same configuration as the watch 300 described with reference to FIGS. 3A and 3B, except for the configuration of the UV LED units 420 for counterfeit detection. Thus, the following descriptions will be focused on the difference in FIGS. 4A and 4B from FIGS. 3A and 3B, in order to exclude duplicate descriptions.

Referring to FIGS. 4A and 4B, one UV LED unit 420 for counterfeit detection may include a first PCB 322a arranged over the bottom part of the main body frame 312 and a first UV LED package 324a mounted on the first PCB 322a. The first UV LED package 324a may include a package board and a first UV LED chip coupled to the package board through a flip chip process in a flip chip configuration or structure. In another embodiment, the first UV LED chip may be directly mounted on the first PCB 322a without the package board. The first UV LED chip may provide UV light at a wavelength of about 300 nm to 420 nm.

Furthermore, another UV LED unit 420 for counterfeit detection may include a second PCB 322b arranged on a sidewall of the main body frame 312 and a second UV LED package 324b mounted on the second PCB 322b. The second UV LED package 324b may include a package board and a second UV LED chip coupled to the package board through a flip chip process in a flip chip configuration or structure. In another embodiment, the second UV LED chip may be directly mounted on the second PCB 322b without the package board. The second UV LED chip may provide UV light at a wavelength of about 300 nm to 420 nm.

In the present embodiment, the first UV LED chip may emit UV light for counterfeit detection toward the top of the watch 400. Thus, a user may irradiate the UV light from the first UV LED chip onto a target bill, and determine whether the target bill is counterfeit or not. Furthermore, the second UV LED chip may emit the UV light toward the number board 314a and the clock hands 314b, and perform the function of a lighting device for illumination, and, in addition, the second UV LED chip may also provide the UV light for counterfeit detection to increase the intensity of UV light with the first UV LED chip. The inclusion of both the first UV LED chip and the second UV LED chip that emit UV light in two different directions provides two different functions and convenience to the user.

In a specific embodiment, the second UV LED chip may be referred to as a black light, for example, and emit UV light in a wavelength region close to the visible light region, the UV light reacting with a fluorescent material. Correspondingly, the number board 314a or the clock hand 324b may be coated with a fluorescent material 315 reacting with the UV light. In response to the UV light emitted from the second UV LED chip, the fluorescent material 315 may emit light in the visible region such that a user can read information of the number board 314a or the clock hand 324b. The fluorescent material 315 may be applied onto at least a part of the number board 314a and the clock hand 324b.

According to a user's selection, the second UV LED chip may be turned on/off separately from the first UV LED chip, and the light intensity of the second UV LED chip may be controlled separately from that of the first UV LED chip. Thus, when the function of the lighting device or illumination is desired, only the second UV LED chip may be operated to emit light. Similarly, when the function of the counterfeit detection is desired, only the first LED chip may be operated to emit light to perform the counterfeit detection.

In another aspect, the disclosed technology provides a method for performing counterfeit detection of currency bills by using a wearable device. This method includes operating one or more LED units in the wearable device to emit UV light at a wavelength that reacts with a fluorescent material embedded in a pattern in an object to cause the fluorescent material to emit fluorescent light as an indication of the object being authentic in counterfeit detection; and controlling a controller of the wearable device to turn on the one or more LED units to activate the counterfeit detection, and to turn off the one or more LED units to turn off the counterfeit detection.

In one implementation of the above method, the wearable device can include a first LED unit that is positioned to emit UV light along a first direction and a second LED unit that is positioned to emit UV light along a second, different direction, a fluorescent part that reacts to the UV light to emit visible fluorescent light and is located in a path of the UV light in the second direction. In this implementation, the method can further include operating the controller to turn on the first LED unit to produce UV light for counterfeit detection of an object placed at a path along the first direction; and operating the controller to turn on the second LED unit to produce UV light for providing illumination by emission of the visible fluorescent light by the fluorescent part in the wearable device. The wearable device may be a watch in which the fluorescent part is part of a display panel of the watch that displays time information, or the fluorescent part includes a clock hand of the watch that displays time information.

Only a few embodiments, implementations and examples are described and other embodiments and implementations, and various enhancements and variations can be made based on what is described and illustrated in this document.

What is claimed is:

1. A watch with a counterfeit detection function, comprising:
   a display panel configured to display time information;
   a first UV LED unit arranged at an edge part of the display panel and configured to provide UV light away from the display panel and towards outside of the watch which reacts with a fluorescent material embedded in a pattern in an object to cause the fluorescent material to emit fluorescent light as an indication of the object being authentic in counterfeit detection;
   a transparent cover positioned over the display panel so as to transmit and focus the UV light;
   a second UV LED unit oriented to provide illumination towards the display panel; and a controller in communication with the first UV LED unit and the second UV LED unit, the controller configured to control the first UV LED unit separately from the second UV LED unit to provide the counterfeit detection and the illumination separate from each other.

2. The watch of claim 1, wherein the first UV LED unit includes: a printed circuit board (PCB) arranged over a support board at the edge part; and a UV LED chip mounted on the PCB to emit the UV light.

3. The watch of claim 2, wherein:
the first UV LED chip is coupled to a package board in a flip chip structure, and the first UV LED chip and the package board are mounted as a package on the PCB.

4. The watch of claim 2, wherein:
the first UV LED unit is arranged on the top surface of the support board as a counterfeit detection device; and
wherein the second UV LED chip is arranged on a side surface of the support board for providing the illumination.

5. The watch of claim 4, wherein:
the second UV LED chip is placed to emit UV light toward a side surface of the display panel, and
the display panel includes a fluorescent material reacting with the UV light from the second UV LED chip to emit fluorescent light to provide illumination.

6. The watch of claim 1, wherein the first UV LED unit provides UV light at a wavelength of 300 nm to 420 nm.

7. The watch of claim 1, wherein a part of the transparent cover positioned over the first UV LED unit is structured to serve as a lens for focusing the UV light.

8. The watch of claim 1, wherein the controller is configured to selectively turn on or off each of the first UV LED unit and the second UV LED unit.

9. A watch with a counterfeit detection function, comprising:
a main body including a display panel that displays information including time and a support board arranged at an edge part of the display panel;
two or more UV LED units arranged on different surfaces of the support board and configured to irradiate UV light in different directions away from the display panel and toward outside of the watch, the UV light reacting with a fluorescent material embedded in a pattern in an object to cause the fluorescent material to emit fluorescent light as an indication of the object being authentic in counterfeit detection;
another UV LED unit oriented to provide illumination towards the display panel; and
a controller in communication with the two or more UV LED unit that enable the indication of the object being authentic in counterfeit detection and the other UV LED unit that provides the illumination, the controller configured to control the two or more UV LED units that enables the indication of the object being authentic in counterfeit detection separate from the other UV LED unit that provides the illumination.

10. The watch of claim 9, wherein the UV LED units include:
a first PCB arranged on the top surface of the support board;
a first UV LED chip in a flip chip configuration mounted on the first PCB; a second PCB arranged on a side surface of the support board; and
a second UV LED chip in a flip chip configuration mounted on the second PCB.

11. The watch of claim 9, wherein the controller is arranged on a sidewall of the main body and configured to control operation of the two or more UV LED units separate from the other UV LED to turn on and off the two or more UV LED units separate from the other UV LED.

12. The watch of claim 9, wherein the UV LED unit provides UV light at a wavelength of 300 nm to 420 nm.

13. The watch of claim 9, wherein the display panel includes:
a number board; and
clock hands arranged on the number board and coated with a fluorescent material that emits fluorescent light when illuminated by the UV light.

14. A watch with a counterfeit detection function, comprising:
a digital display panel that displays digital information including time;
a support coupled to support the display panel;
UV LED units mounted on the support and located outside the digital display panel, each UV LED unit operable to emit UV light away from the display panel and toward outside the watch at a wavelength that reacts with a fluorescent material embedded in a pattern in an object to cause the fluorescent material to emit fluorescent light as an indication of the object being authentic in counterfeit detection;
a controller mounted to a side of the support and coupled to control operations of the digital display and the UV LED units; and
another UV LED unit in communication with the controller and configured to provide illumination towards the display panel;
wherein the controller is configured to control the UV LED units that enable the indication of the object being authentic in counterfeit detection separate from the other UV LED unit that provides the illumination to separately control the counterfeit detection and illumination.

15. The watch of claim 14, wherein:
the UV LED units are mounted on different surfaces of the support to emit UV light in different directions to allow for counterfeit detection.

16. The watch of claim 14, wherein:
at least part of the digital display panel includes a fluorescent material that reacts with the UV light to emit visible fluorescent light that provides illumination.

17. The watch of claim 16, wherein:
one of the UV LED units is mounted at a first location to emit UV light away from the digital display panel; and
another of the UV LED units is mounted at a second location to emit UV light towards the part of the digital display panel that includes the fluorescent material to cause illumination by emission of visible fluorescent light by the fluorescent material.

* * * * *